(12) United States Patent
Chung et al.

(10) Patent No.: US 9,937,655 B2
(45) Date of Patent: Apr. 10, 2018

(54) METHOD OF MANUFACTURING CATHETER FOR ANTIMICROBIAL CONTROL

(75) Inventors: Kenneth K. Chung, Denver, CO (US); Anthony B. Brennan, Gainesville, FL (US); Mark McCullough Spiecker, Centennial, CO (US); Ryan Stoneberg, Chicago, IL (US); Walter Scott Thielman, Palatine, IL (US); Shravanthi Reddy, Denver, CO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 569 days.

(21) Appl. No.: 13/161,137

(22) Filed: Jun. 15, 2011

(65) Prior Publication Data
US 2012/0319325 A1 Dec. 20, 2012

(51) Int. Cl.
*B29C 59/04* (2006.01)
*B29C 59/02* (2006.01)
(Continued)

(52) U.S. Cl.
CPC ....... *B29C 59/043* (2013.01); *A61M 25/0009* (2013.01); *A61M 25/0013* (2013.01);
(Continued)

(58) Field of Classification Search
CPC .......... A61M 25/0009; A61M 25/0013; A61M 25/0023; A61M 2025/006; B29C 49/0015;
(Continued)

(56) References Cited

U.S. PATENT DOCUMENTS 3,243,850 A  4/1966  Zieg
3,351,441 A  11/1967  Gewiss et al.
(Continued)

FOREIGN PATENT DOCUMENTS

BE  1008153 A7  1/1996
CA  2368204      3/2000
(Continued)

OTHER PUBLICATIONS

European Search Report for Appl. 12172148.4 dated Nov. 23, 2012, 13 pages.
(Continued)

*Primary Examiner* — Benjamin A Schiffman
(74) *Attorney, Agent, or Firm* — Alston & Bird LLP (57) ABSTRACT

Disclosed herein is a method comprising transporting a conduit and a template through a guide tube; the template being disposed on an outer surface of the conduit between the conduit and the guide tube; and transferring a texture from the template to the conduit as the conduit and the template are transported through the guide tube. Disclosed herein too is an apparatus comprising a guide tube; the guide tube being operative to facilitate a transfer of a pattern from a template to a conduit; a first feed spool and a first take-up spool for feeding the conduit through the guide tube and for taking up the conduit after it has travelled through the guide tube respectively; and a second feed spool and a second take-up spool for feeding the template through the guide tube and for taking up the template after it has travelled through the guide tube respectively.

7 Claims, 4 Drawing Sheets

(51) Int. Cl.
*A61M 25/00* (2006.01)
*B29C 35/02* (2006.01)
*B29C 35/08* (2006.01)

(52) U.S. Cl.
CPC ....... *A61M 25/0023* (2013.01); *B29C 59/021* (2013.01); *B29C 59/022* (2013.01); *A61M 2025/006* (2013.01); *B29C 35/02* (2013.01); *B29C 2035/0822* (2013.01); *B29C 2035/0827* (2013.01); *B29C 2035/0844* (2013.01); *B29C 2035/0855* (2013.01); *B29C 2035/0861* (2013.01); *B29C 2035/0877* (2013.01)

(58) Field of Classification Search
CPC ... B29C 59/043; B29C 59/021; B29C 43/224; B29C 59/022
See application file for complete search history.

(56) References Cited

U.S. PATENT DOCUMENTS

| | | |
|---|---|---|
| 3,354,022 A | 11/1967 | Dettre et al. |
| 3,795,471 A * | 3/1974 | Milani .................. 425/388 |
| 3,935,485 A | 1/1976 | Yoshida et al. |
| 3,971,084 A | 7/1976 | Spier |
| 3,992,162 A | 11/1976 | Gewiss |
| 3,996,323 A | 12/1976 | Hegler et al. |
| 4,101,625 A | 7/1978 | Haley |
| 4,283,461 A | 8/1981 | Wooden et al. |
| 4,284,689 A | 8/1981 | Craighead et al. |
| 4,297,394 A | 10/1981 | Wooden et al. |
| 4,637,743 A | 1/1987 | Kerner et al. |
| 4,640,859 A | 2/1987 | Hansen et al. |
| 4,655,986 A * | 4/1987 | Cothran et al. ............. 264/508 |
| 4,865,603 A | 9/1989 | Noiles |
| 5,008,140 A | 4/1991 | Schmertz |
| 5,028,474 A | 7/1991 | Czaplicki |
| 5,328,200 A | 7/1994 | Pelizzari |
| 5,344,691 A | 9/1994 | Hanschen et al. |
| 5,403,680 A | 4/1995 | Otagawa et al. |
| 5,645,764 A | 7/1997 | Angelopoulos et al. |
| 5,650,214 A | 7/1997 | Anderson et al. |
| 5,842,937 A | 12/1998 | Dalton et al. |
| 5,971,326 A | 10/1999 | Bechert |
| 5,976,284 A | 11/1999 | Calvert et al. |
| 6,010,442 A | 1/2000 | Lemons et al. |
| 6,075,585 A | 6/2000 | Minne et al. |
| D430,734 S | 9/2000 | Bredendick et al. |
| D436,738 S | 1/2001 | Bredendick et al. |
| D440,051 S | 4/2001 | Bredendick et al. |
| 6,231,463 B1 | 5/2001 | Tavares et al. |
| D443,766 S | 6/2001 | Bredendick et al. |
| 6,394,652 B2 | 5/2002 | Meyer et al. |
| D459,897 S | 7/2002 | Bredendick et al. |
| 6,458,447 B1 | 10/2002 | Cabell et al. |
| 6,569,038 B2 | 5/2003 | Sullivan |
| 6,616,882 B1 | 9/2003 | Lidgett |
| 6,660,363 B1 | 12/2003 | Barthlott |
| 6,686,026 B2 | 2/2004 | Spiewak et al. |
| 6,911,243 B2 | 6/2005 | Sher et al. |
| 6,946,170 B2 | 9/2005 | Gerber et al. |
| D518,648 S | 4/2006 | Broering et al. |
| 7,117,536 B2 | 10/2006 | Burnett et al. |
| 7,117,807 B2 | 10/2006 | Bohn, Jr. et al. |
| 7,143,709 B2 | 12/2006 | Brennan et al. |
| 7,303,491 B2 | 12/2007 | Nardacci et al. |
| 7,650,848 B2 | 1/2010 | Brennan et al. |
| 7,691,464 B2 | 4/2010 | Gerber et al. |
| 8,075,298 B2 * | 12/2011 | Nielsen et al. ............. 425/385 |
| 2002/0150724 A1 | 10/2002 | Nun et al. |
| 2003/0228445 A1 | 12/2003 | Vaughn et al. |
| 2004/0086674 A1 | 5/2004 | Holman |
| 2004/0191538 A1 | 9/2004 | Huang |
| 2005/0003146 A1 | 1/2005 | Spath |
| 2005/0008828 A1 | 1/2005 | Libera et al. |
| 2005/0119723 A1 | 6/2005 | Peacock, III |
| 2005/0119758 A1 | 6/2005 | Alexander et al. |
| 2005/0136217 A1 | 6/2005 | Barthlott et al. |
| 2005/0178286 A1 | 8/2005 | Bohn, Jr. et al. |
| 2006/0219143 A1 | 10/2006 | Brennan et al. |
| 2007/0098957 A1 | 5/2007 | Barthlott et al. |
| 2007/0227428 A1 * | 10/2007 | Brennan et al. ............. 114/67 R |
| 2008/0000375 A1 * | 1/2008 | Nielsen et al. ............. 101/450.1 |
| 2008/0202370 A1 | 8/2008 | Muraoka |
| 2008/0250949 A1 | 10/2008 | Hanzel |
| 2009/0185023 A1 | 7/2009 | Higuchi et al. |
| 2010/0033818 A1 | 2/2010 | Petcavich |
| 2010/0119755 A1 | 5/2010 | Chung |
| 2010/0226943 A1 | 9/2010 | Brennan |

FOREIGN PATENT DOCUMENTS

| | | |
|---|---|---|
| DE | 403375 A | 9/1924 |
| DE | 3801139 C1 | 9/1988 |
| DE | 19613304 A1 | 10/1997 |
| DE | 19840303 A1 | 3/2000 |
| DE | 20115718 U1 | 11/2002 |
| EP | 0015312 A1 | 9/1980 |
| EP | 1469198 A1 | 10/2004 |
| FR | 2735720 B1 | 8/1997 |
| GB | 722591 | 1/1955 |
| GB | 1100423 A | 1/1968 |
| GB | 1536178 A | 12/1978 |
| GB | 2207389 B | 4/1990 |
| JP | S52-115670 U | 9/1977 |
| JP | H4-11620 U | 1/1992 |
| JP | H10-118188 A | 5/1998 |
| JP | 2001207123 | 7/2001 |
| WO | WO9302517 | 12/1993 |
| WO | WO9604123 | 2/1996 |
| WO | WO 1997/003810 A1 | 2/1997 |
| WO | WO0058410 | 10/2000 |
| WO | WO2006026993 | 3/2006 |
| WO | 2008070625 A2 | 6/2008 |
| WO | WO2008070625 | 6/2008 |
| WO | WO 2010/056824 A2 | 5/2010 |
| WO | WO 2011/017074 A1 | 2/2011 |

OTHER PUBLICATIONS

Patent Examination Report for Australian Application No. 2012203477 dated Aug. 19, 2016.
Patent Abstract of Japan; Publication No. 10-123693; May 15, 1998 (1 page).
Patent Abstracts of Japan; 62-046232 dated Feb. 28, 1987—(1 page).
A. Tuteja, et al. "Designing Superoleophobic Surfaces" Science (Dec. 7, 2007) pp. 1618-1622, ScienceMag.org.
B. He, et al. "Multiple Equilibrium Droplet Shapes and Design Criterion for Rough Hydrophobic Surfaces", Langmuir (2003) pp. 4999-5003, vol. 19; American Chemical Society.
Callow et al. "Primary adhesion of enteromorpha (chlorophyta, ulvales) propagules: quantitative settlement studies and video microscopy", J. Phycol., 1997, vol. 33 pp. 938-947.
Cassie et al. "Wettability of porous surfaces", Trans. Faraday Society, 1944, vol. 40, pp. 546-551.
D. Quere "Wetting and Roughness" Annu. Rev. Mater. Res. (2008) pp. 71-99 vol. 38, Annual Reviews.
D.M. Spori, et al. "Beyond the Lotus Effect: Roughness Influences on Wetting Over a Wide Surface-Energy Range" Langmuir (2008) pp. 5411-5417, vol. 24, American Chemical Society.
D.W. Bechert, et al. "Fluid Mechanics of Biological Surfaces and their Technological Application", Naturwissenschaften (2000) pp. 157-171; vol. 87; Springer-Verlag, Germany.
E. Martines, et al. "Superhydrophobicity and Superhydrophilicity of Regular Nanopatterns" Nano Letters (2005) pp. 2097-2103, vol. 5, No. 10, American Chemical Society.
Fractals Are Smart: Fractal Pack 1 Educators' Guide. Downloaded from the FractalFoundation.org. Copyright 2009.

(56) References Cited

OTHER PUBLICATIONS

G. McHale, et al. "Analysis of Droplet Evaporation on a Superhydrophobic Surface" Langmuir (2005) pp. 11053-11060, vol. 21, American Chemical Society.

H.C. Flemming, "Biofouling in Water Systems—Cases, Causes and Countermeasures", Appl. Microbiol Biotechnol (2002), pp. 629-640, vol. 59; Springer-Verlag, Germany.

Horiuchi et al. "Optical lithography onto inside surfaces of small-diameter pipes" Microelectronic Engineering 85 (2008) 1043-1046—Elsevier.

International Search Report dated Jun. 13, 2006 for Application No. PCT/US05/04972—4 pages.

International Search Report dated May 22, 2008 for Application No. PCT/US07/86289—10 pages.

J. Bico, et al. "Wetting of Textured Surfaces", Colliods and Surfaces (2002) pp. 41-46, vol. 206; Elsevier Science B.V.

J. Bico, et al. "Pearl Drops" Europhysics Letters (Jul. 15, 1999) pp. 220-226; vol. 47 (2); EDP Sciences.

J. Genzer et al. "Recent Developments in Superhydrophobic Surfaces and their Relevance to Marine Fouling: A Review" Biofouling (2006) pp. 1-22, Taylor & Francis.

J.M. Hills, et al. "Settlement of Barnacle Larvae is Governed by Euclidean and not Fractal Surface Characteristics" Functional Ecology (1999), pp. 868-875, vol. 13, British Ecological Society.

L.D. Chambers, et al. "Modern Approaches to Marine Antifouling Coatings" Surface and Coatings Technology (2006) pp. 3642-3652, vol. 201, Elsevier B.V.

M.E. Abdelsalam, et al. "Wetting of Regularly Structured Gold Surfaces" Langmuir (2005) pp. 1753-1757, vol. 21, American Chemical Society.

M.E. Callow, et al. "Microtopographic Cues for Settlement of Zoospores of the Green Fouling Alga Enteromorpha", Biofouling (2002) pp. 237-245; vol. 18 (3); Taylor & Francis, UK.

Quere "Rough ideas on wetting", Physica A, 2002 vol. 313, pp. 32-46.

R. Furstner, et al. "Wetting and Self-Cleaning Properties of Artificial Superhydrophobic Surfaces", Langmuir (2005), pp. 956-961, vol. 21; American Chemical Society.

Search Report dated Jun. 25, 2010 for Application No. PCT/US09/064160—8 pages.

Machine Translation of JP 05-010309 A, Oct. 15, 2013.

W.R. Hansen, et al. "Evidence for Self-Cleaning in Gecko Setae" Evolution (Jan. 11, 2005) pp. 385-389, vol. 102 vol. 2; PNAS.

Wenzel "Resistance of solid surfaces to wetting by water", Industrial and Engineering Chemistry, 1936, vol. 28, No. 8, pp. 988-994.

Written Opinion dated Jun. 13, 2006 for Application No. PCT/US05/04972—6 pages.

Written Opinion dated May 22, 2008 for Application No. PCT/US07/86289—6 pages.

Written Opinion dated Jun. 25, 2010 for Application No. PCT/US09/064160—6 pages.

Xia et al. "Soft Lithography", Annu. Rev. Mater. Sci., 1998, vol. 28, pp. 153-184.

Y. Chen, et al. "Anisotropy in the Wetting of Rough Surfaces", Journal of Colloid and Interface Sciences (2005), pp. 458-464, vol. 281; Elsevier Inc.

Z. Burton, et al. "Hydrophobicity, Adhesion, and Friction Properties of Nanopatterned Polymers and Scale Dependence for Micro- and Nanoelectromechanical Systems" Nano letters (2005) pp. 1607-1613, vol. 5 No. 8, American Chemical Society.

\* cited by examiner

Figure 4D

METHOD OF MANUFACTURING CATHETER FOR ANTIMICROBIAL CONTROL

BACKGROUND

Disclosed herein is a catheter for antimicrobial control and methods of manufacturing thereof.

Surfaces that have patterns and other forms of texturing (hereinafter "texturing") can be advantageously used to minimize the adhesion of living organisms and other forms of non-living matter (e.g., ice, dust, dirt, and the like) to the surface. The texturing can have dimensions that are selected to specifically prevent the adhesion of specific living organisms or non-living matter on the surface, while at the same time encouraging the growth of other organisms or the adhesion of other types of non-living matter to the surface.

For example, in order to prevent the growth of certain types of living organisms the dimensions of the texturing may have to be in the nanometer or in the micrometer range, while for preventing the growth of certain other types of organisms, the dimensions of the texturing may have to be in the millimeter or centimeter range. In another example, in order to facilitate the growth of certain types of living organisms the dimensions of the texturing may have to be in the nanometer or in the micrometer range, while for facilitating the growth of certain other types of organisms, the dimensions of the texturing may have to be in the millimeter or centimeter range. Reproducing this texturing on surfaces that are large in size (e.g., of the area of several square centimeters) or on surfaces that have a complex shape (e.g., a non-planar surface that is circular or spherical) is difficult.

It is therefore desirable to have methods that can reproduce the texturing on catheters that have large surface areas relative to the area of the pattern. It is also desirable to reproduce the texturing on surfaces that have complex shapes or disposed upon surfaces located in regions that are difficult to access.

SUMMARY

Disclosed herein is a method comprising transporting a conduit and a template through a guide tube; the template being disposed on an outer surface of the conduit between the conduit and the guide tube; and transferring a texture from the template to the conduit as the conduit and the template are transported through the guide tube.

Disclosed herein is an apparatus comprising a guide tube; the guide tube being operative to facilitate a transfer of a pattern from a template to a conduit; a first feed spool and a first take-up spool for feeding the conduit through the guide tube and for taking up the conduit after it has travelled through the guide tube respectively; and a second feed spool and a second take-up spool for feeding the template through the guide tube and for taking up the template after it has travelled through the guide tube respectively.

Disclosed herein too is a method comprising disposing a texture on a curved surface of a conduit; the texture comprising a plurality of patterns; each pattern being defined by a plurality of spaced apart features attached to or projected into the curved surface, the plurality of features each having at least one neighboring feature having a substantially different geometry, wherein an average spacing between adjacent spaced apart features is about 1 nanometer to about 1 millimeter in at least a portion of the curved surface, wherein the plurality of spaced apart features are represented by a periodic function; and disposing the conduit in a body of a living being.

DETAILED DESCRIPTION

It is to be noted that as used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges disclosed herein are inclusive of the endpoints and independently combinable.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition phrase "comprising" is inclusive of the transition phrases "consisting essentially of" and "consisting of".

Disclosed herein is a conduit that comprises a texture. The texture is disposed on a surface of the conduit. The surface of the conduit upon which the texture is disposed is generally an outer surface. In an exemplary embodiment, the texture is disposed upon an outer surface of the conduit. The texture can be used to control bioadhesion on the conduit. In one embodiment, the texturing can be used to minimize the adhesion of living or non-living matter, while in another embodiment, the texturing can be used to increase the adhesion of living or of non-living matter.

Disclosed herein too is a method for manufacturing the conduit by transferring a texture from a template to the conduit. In an exemplary embodiment, the template is disposed between a guide tube and the conduit in a continuous process and transfers its pattern to the conduit upon the application of pressure to the conduit. During the travel of the conduit through the guide tube, pressure is applied to the template to transfer a texture contained on the template to the outer surface of the conduit. This method of manufacturing permits the texturing of large surfaces that have complex non-planar surfaces.

Figure 1:
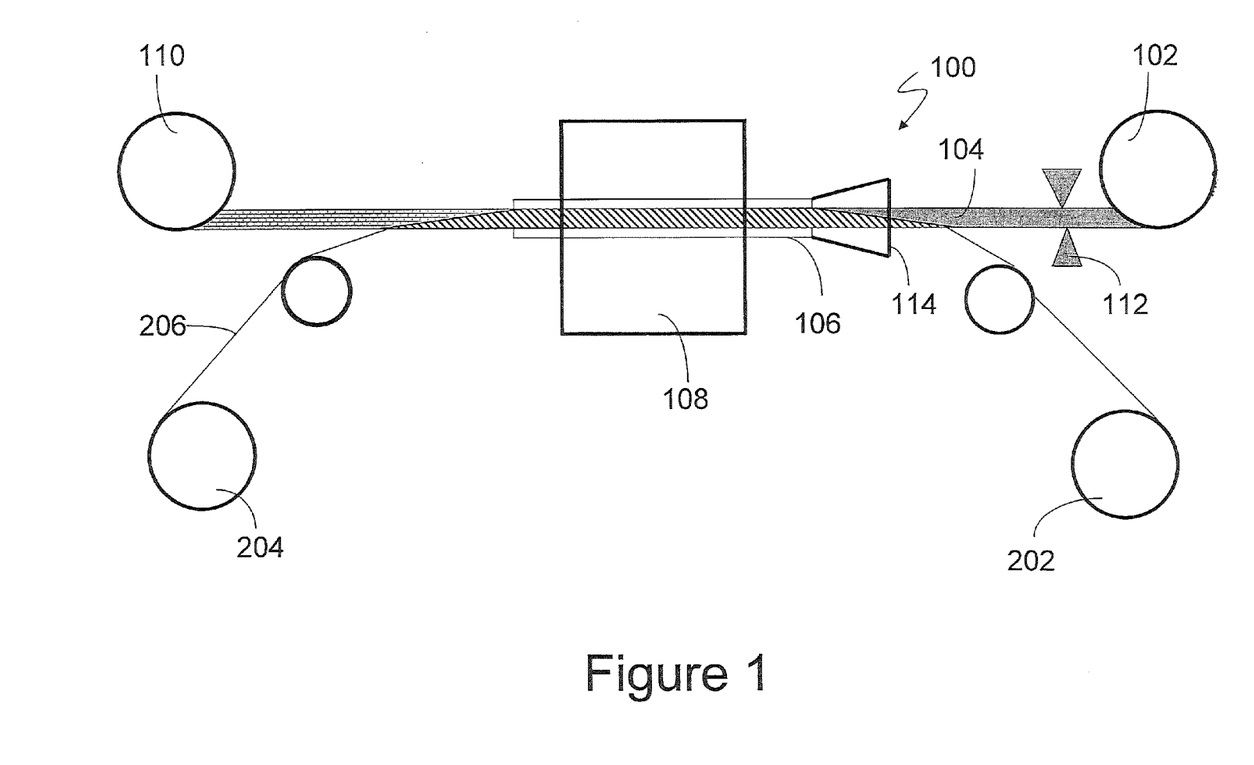
FIG. 1 depicts an exemplary method of manufacturing the textured conduit.

With reference now to the FIG. 1, an apparatus 100 for texturing the conduit comprises a first feed spool 102 for feeding the conduit 104 towards a guide tube 106 and an optional curing chamber 108. The conduit 104 is wound around a first take-up spool 110 after being fed through the guide tube 106 and the curing chamber 108. The apparatus 100 also comprises a second feed spool 202 and a second take-up spool 204 for feeding the template 206 and taking up the template 206 respectively. The template 206 contains an opposing image of the texture to be transmitted to the guide tube 106. An optional centering device 112 may be used to accurately feed the conduit to the guide tube 106.

In one method of using the apparatus 100, the conduit 104 is fed from the first feed spool 102 through the guide tube 106 and the curing chamber 108 and taken up by the first take-up spool 110. At the same time the template 206 is fed from the second feed spool 202 through the guide tube 106 and the curing chamber 108 to the second take-up spool 204. During the travel from the second feed spool 202 to the second take-up spool 204, the template 206 is wrapped around a portion of the conduit 104. In one embodiment, the template 206 is wrapped around the entire circumference of the conduit 104 that is present in the guide tube 106. A conical guide 114 in communication with the guide tube 106 facilitates the guiding of the conduit 104 into the guide tube 106. The conical guide 104 also facilitates the wrapping of the template 206 around the conduit 104.

As the conduit 104 with the template 206 wrapped thereon passes through the guide tube 106, the pressure between the conduit 104 and the guide tube 106 causes the template to transfer an image of the desired texture to the conduit 104. After transferring the image to the conduit 104, the template is removed from the conduit 104 and rewound around the second take-up spool 204.

Figure 2:
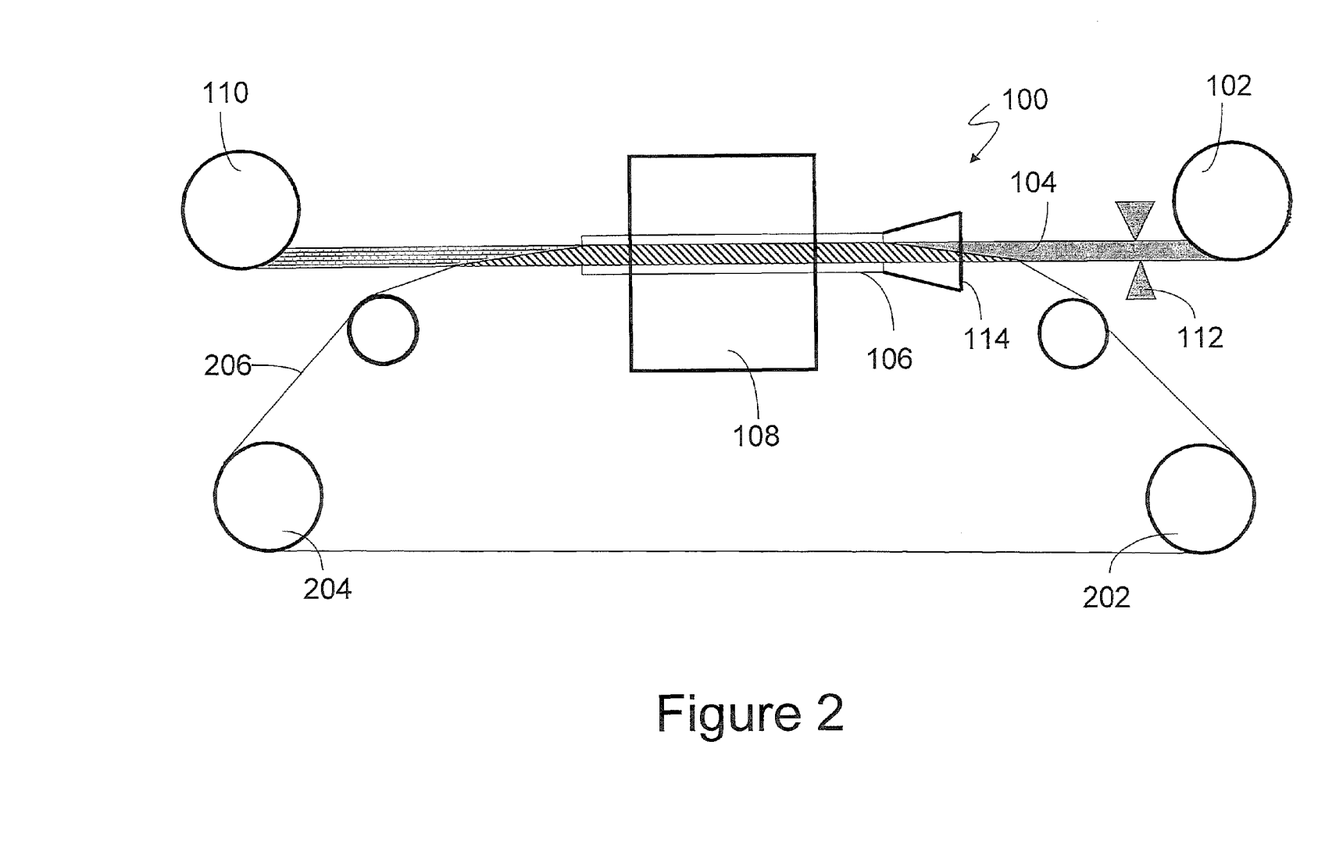
FIG. 2 another exemplary method of manufacturing the textured conduit.
Figure 3:
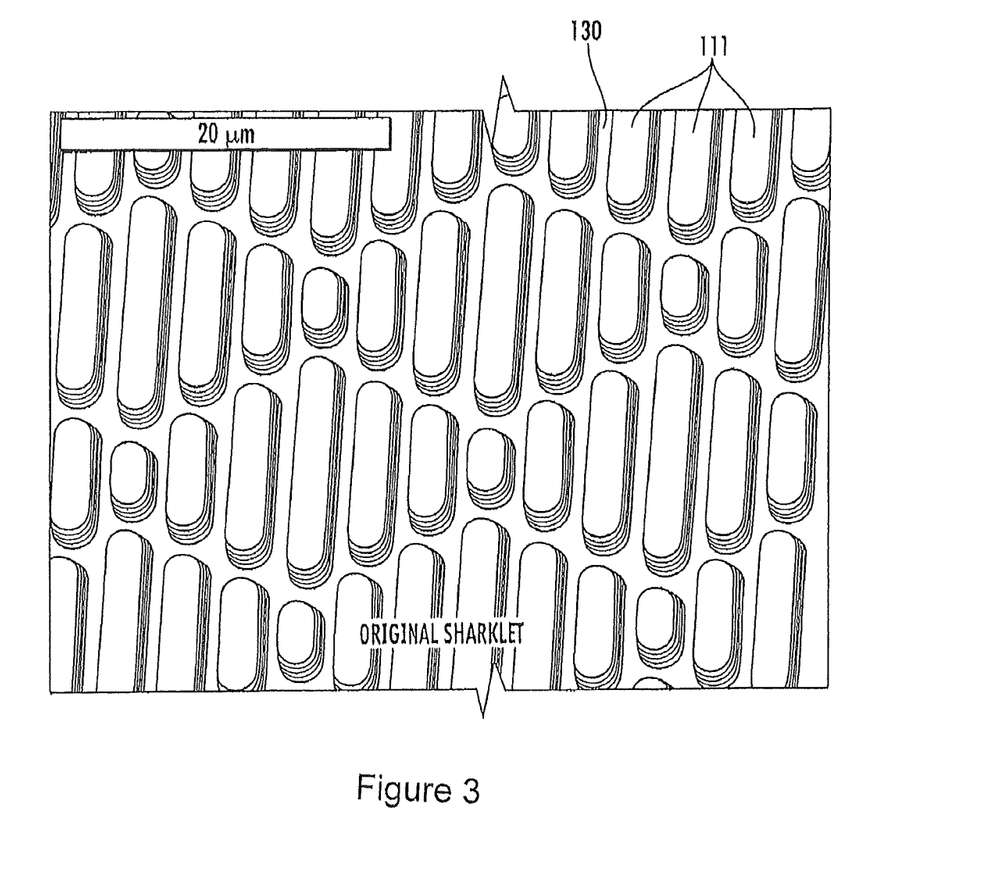
FIG. 3 is an example of the texture comprising a plurality of patterns.
Figure 4A:
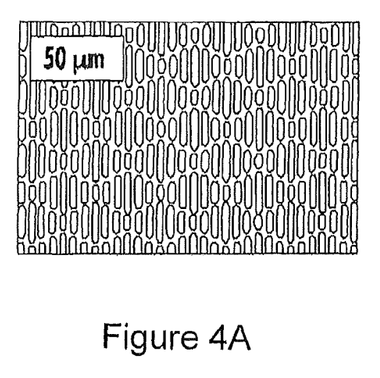
FIG. 4A-4D is another example of the texture that comprises a plurality of patterns.
Figure 4B:
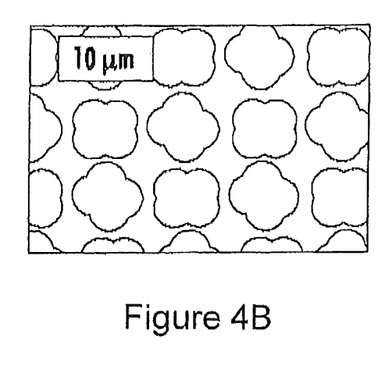
Figure 4C:
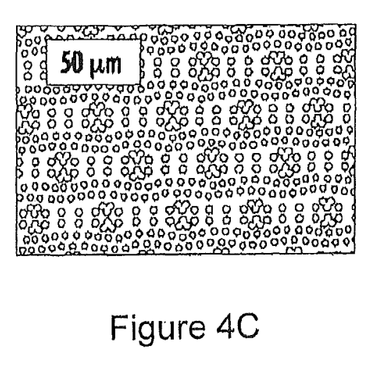
Figure 4D:
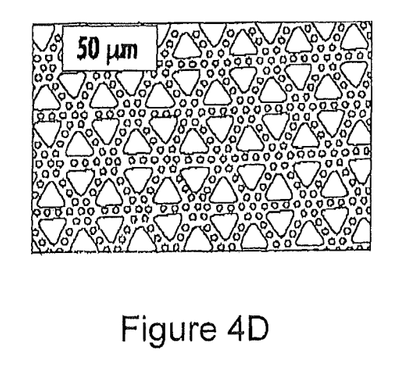

In an exemplary embodiment depicted in the FIG. 2, the template 206 is a continuous belt that continuously travels around the second feed spool 202 and the second take-up spool 204 and contacts the conduit 104 during its travel through the guide tube 106.

During the travel of the conduit 104 and the template 206 through the guide tube 106, pressure may be applied to the conduit, the template and/or to the guide tube 106 to transfer the texture to the conduit. In one embodiment, the pressure may be applied by pressurizing the conduit 104. Pressurizing the conduit 104 can be accomplished by increasing the fluid pressure within the conduit 104, forcing the conduit 104 radially outwards against the guide tube 106 thereby facilitating a transfer of the image from the template 206 to the conduit 104 as a result of the pressure. Fluids used within the conduit 104 may include air, water, magneto-rheological fluids and electro-rheological fluids. When magneto-rheological or electro-rheological fluids are used, the use of magnetic field or an electrical field respectively may be used to increase the stiffness of the conduit 104, thereby increasing the pressure between the guide tube 106 and the conduit 104 resulting in a transfer of the image from the template 206 to the conduit 104.

The pressure in the conduit may be about 0.01 to about 1.0 kilograms per square centimeter. A preferred pressure in the conduit is about 0.09 to about 0.45 kilograms per square centimeter.

In another embodiment, a solid mandrel (not shown) that has a higher stiffness than the guide tube may be disposed inside the conduit 104 during the travel of the conduit 104 through the guide tube 106. The use of a mandrel promotes an increase in pressure between the guide tube 106 and the conduit 104 resulting in a transfer of the image from the template 206 to the conduit 104. The mandrel may be hollow or have a solid core, but has a higher stiffness than the guide tube.

In yet another embodiment, the template 206 may be manufactured in the form of a balloon (i.e., a tube similar to a bicycle tube that can wrap itself around the conduit, but from which air cannot escape without intervention). During the passage through the guide tube 106, the pressure within the template 206 is increased resulting in a transfer of the image from the template 206 to the conduit 104. Fluids used within the template 206 may include air, water, magnetorheological fluids and electro-rheological fluids.

The guide tube 106 can be manufactured from a metal, a ceramic or a polymer. In one embodiment, the guide tube is manufactured from a metal and has a low friction polymeric coating disposed on the inner surface thereof. Examples of low friction polymeric coatings include polymers that comprise polydimethylsiloxane and/or fluoropolymers.

In one embodiment, the guide tube is manufactured from a piezoelectric material that can have an electric field applied to it during the travel of the conduit and the template through it. Piezoelectric materials can change their dimensions upon the application of an electric field and conversely can generate an electric field when pressure is applied to the piezoelectric material. By applying an electric field to the guide tube, radial pressure can be applied by the guide tube to the template which then transfers an opposing image to the conduit.

The guide tube 106 may be heated using resistive heating, electromagnetic radiation or a combination of resistive heating and electromagnetic radiation. The curing chamber 108 may be used to cure (crosslink) any reactive species on the conduit 104. The crosslinking can be accomplished using radiation (e.g., ultraviolet, infrared, microwave, radiofrequency, electron beam, xrays, or the like) or by heating. Curing can improve chemical resistance and/or thermal resistance of the conduit.

The conduit 104 may comprise a metal, a ceramic an organic polymer, or a combination comprising at least one of a metal, a ceramic, or an organic polymer. The organic polymer may comprise a glassy polymer (i.e., a polymer that is below its glass temperature at the temperature of the human body), an elastomer (a polymer that is above its temperature at the temperature of the human body), an amorphous polymer or a semicrystalline polymer. Organic polymers may comprise thermosets, thermoplastics or a combination comprising at least one of a thermoset or a thermoplastic. The organic polymer may comprise a block copolymer, a diblock copolymer, a star block copolymer, a triblock copolymer, a dendrimer, an ionic copolymer, a polyelectrolyte, or the like. In one embodiment, it is desirable for the conduit to comprise an elastomer.

Examples of thermoplastic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of thermosetting polymers suitable for use in the polymeric composition include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

An exemplary thermoplastic polymer comprises polysiloxane or a fluoropolymer. An exemplary thermosetting polymer comprises polysiloxane or a fluoropolymer.

As noted above, it is desirable for the conduit to be manufactured from an elastomer. Examples of suitable elastomers are polydimethylsiloxane, polybutadiene, polyisoprene, styrene-butadiene-styrene (SBS), styrene-isoprene-styrene (SIS), styrene-ethylene/butylene-styrene (S-EB-S) block copolymers, thermoplastic polyurethanes, copolyester-ethers (block copolymers derived from terephthalic acid, polytetramethylene glycol, and 1,4-butanediol), natural rubber, synthetic polyisoprene, butyl rubber, halogenated butyl rubbers, polybutadiene, styrene-butadiene rubber, nitrile rubber, hydrogenated nitrile rubbers, chloroprene rubber, polychloroprene, ethylene propylene rubber, and ethylene propylene diene rubber, epichlorohydrin rubber, polyacrylic rubber, silicone rubber, fluoro silicone rubber, fluoroelastomers, perfluoroelastomers, polyether-block-polyamides, chlorosulfonated polyethylene, ethylene-vinyl acetate, or the like, or a combination comprising at least on of the foregoing block elastomers. An exemplary elastomer is a polysiloxane. It is desirable for the elastomer to have an elastic modulus of about $10^5$ pascals to about $10^8$ pascals.

The texture comprises a plurality of patterns. In one embodiment, the pattern generally has some features that are of the order of a few nanometers to several hundreds of millimeters in size. Each pattern is defined by a plurality of spaced apart features attached to or projected into the curved surface. The plurality of features on the surface each has at least one neighboring feature that has a substantially different geometry or a substantially different size. The average spacing between adjacent features on the surface is between about 1 nanometer to about 1 millimeter in at least a portion of the curved surface.

In one embodiment, when viewed in a first direction, the plurality of spaced apart features are represented by a periodic function. In another embodiment, the plurality of spaced apart features form a pattern. Each pattern is separated from a neighboring pattern by a pathway that has a periodicity to it. The periodicity of this pathway may be sinusoidal. Examples of the texture are shown in the FIGS. 3, 4A, 4B, 4C and 4D.

In one embodiment, the conduit can comprise a pattern that comprises a plurality of spaced features. The spaced features are arranged in a plurality of groupings. The groupings of features comprise repeat units that can be repeated laterally and longitudinally across the surface. The spaced features within a grouping are spaced apart at an average distance of about 1 nanometer to about 500 micrometers. Each spaced feature has a surface that is substantially parallel to a surface on a neighboring feature. Each feature is separated from a neighboring feature and the groupings of features are arranged with respect to one another so as to define a tortuous pathway.

In yet another embodiment, the conduit comprises a plurality of spaced features. The features are arranged in a plurality of groupings such that the groupings of features comprise repeat units. The spaced features within a grouping are spaced apart at an average distance of about 1 nanometer to about 500 micrometers. The groupings of features are arranged with respect to one another so as to define a tortuous pathway where a tangent to the tortuous pathway intersects with a spaced feature. The spaced feature is different in geometry (shape or size) from each nearest neighbor and is not in contact with the nearest neighbor.

In yet another embodiment, the surface of the conduit has a topography that comprises a pattern defined by a plurality of spaced apart features attached to or projected into a base surface of the device (i.e., the base surface of the conduit). The plurality of features comprise at least one feature having a substantially different geometry, wherein neighboring patterns share a common feature, the plurality of spaced apart features having at least one dimension that is about 1 nanometer to about 1,000 micrometers. The neighboring spaced apart features can be spaced apart by a distance of about 5 nanometers to about 500 micrometers, specifically about 10 nanometers to about 100 micrometers, specifically about 1 micrometer to about 50 micrometers, and more specifically about 2 micrometers to about 25 micrometers.

In yet another embodiment, the surface after the texturing comprises a plurality of spaced features; the features being arranged in a plurality of groupings; the groupings of features comprising repeat units; the spaced features within a grouping being spaced apart at an average distance of about 1 nanometer to about 200 millimeters; the groupings of features being arranged with respect to one another so as to define a tortuous path. In one embodiment, a tangent to the tortuous path intersects with at least one of the features. In another embodiment, the tortuous path can be represented by a periodic function. The periodic function may be sinusoidal.

In one embodiment, when viewed in a second direction, the pathway between the features may be non-linear and non-sinusoidal. In other words, the pathway can be non-linear and aperiodic. In another embodiment, the pathway between the features may be linear but of a varying thickness. The plurality of spaced features may be projected outwards from a surface or projected into the surface. In one embodiment, the plurality of spaced features may have the same chemical composition as the surface. In another embodiment, the plurality of spaced features may have a different chemical composition from the surface.

In one embodiment, the surface of the conduit is monolithically integrated with the base of the conduit, wherein a composition of the conduit is the same as the composition of the surface of the conduit. In another embodiment, the surface of the conduit comprises a coating layer disposed on the conduit. In yet another embodiment, the composition of the coating layer is different from the composition of the conduit.

In another embodiment, the topography provides an average roughness factor (R) of from 2 to 50. The surface may comprise an elastomer that has an elastic modulus of about 10 kPa to about 10 MPa.

As noted above, the pattern is separated from a neighboring pattern by a tortuous pathway. The tortuous pathway may be represented by a periodic function. The periodic functions may be different for each tortuous pathway. In one embodiment, the patterns can be separated from one another by tortuous pathways that can be represented by two or more periodic functions. The periodic functions may comprise a sinusoidal wave. In an exemplary embodiment, the periodic function may comprise two or more sinusoidal waves.

In another embodiment, when a plurality of different tortuous pathways are represented by a plurality of periodic functions respectively, the respective periodic functions may be separated by a fixed phase difference. In yet another embodiment, when a plurality of different tortuous pathways are represented by a plurality of periodic functions respectively, the respective periodic functions may be separated by a variable phase difference.

In one embodiment, the plurality of spaced apart features have a substantially curved top surface that is concentric with the inner surface of the conduit. In another embodiment, a multi-element plateau layer can be disposed on a portion of the surface of the conduit, wherein a spacing distance between elements of said surface layer provide a second feature spacing; the second feature spacing being substantially different when compared to the first feature spacing.

In one embodiment, each feature of a pattern has at least one neighboring feature that has a different geometry (e.g., size or shape). A feature of a pattern is a single element. Each feature of a pattern has at least 2, 3, 4, 5, or 6 neighboring features that have a different geometry from the feature. In one embodiment, there are at least 2 or more different features that form the pattern. In another embodiment, there are at least 3 or more different features that form the pattern. In yet another embodiment, there are at least 4 or more different features that form the pattern. In yet another embodiment, there are at least 5 or more different features that form the pattern.

In another embodiment, at least two identical features of the pattern have at least one neighboring feature that has a different geometry (e.g., size or shape). A feature of a pattern is a single element. In one embodiment, two identical features of the pattern have at least 2, 3, 4, 5, or 6 neighboring features that have a different geometry from the identical features. In another embodiment, three identical features of the pattern have at least 2, 3, 4, 5, or 6 neighboring features that have a different geometry from the identical features.

In another embodiment, each pattern has at least one or more neighboring patterns that have a different size or shape. In other words, a first pattern can have a second neighboring pattern that while comprising the same features as the first pattern can have a different shape from the first pattern. In yet another embodiment, each pattern has at least two or more neighboring patterns that have a different size or shape. In yet another embodiment, each pattern has at least three or more neighboring patterns that have a different size or shape.

In yet another embodiment, each pattern has at least four or more neighboring patterns that have a different size or shape.

The template can be in the form of a film or in the form of a tube. It is desirable for the film or the tube to be flexible so that it can contact the conduit, be wrapped around it and be removed from it after transferring its texture to the conduit. It is desirable for the template to be wrapped completely around the conduit so that the texture can be transferred to the entire circumferential surface of the conduit. It is also desirable for the template to be reusable.

In one embodiment, a plurality of templates can be used to transfer the texture to the conduit. For example, the lower half of the conduit can be textured by a first template while the upper half of the conduit can be textured by a second template. In a similar manner, three or four different templates can contact different portions of the conduit and transfer the texture to the conduit.

The template can comprise a polymer (e.g., those polymers listed above), or a metal or ceramic that is flexible enough to be wrapped around the conduit and unwrapped from the conduit upon completion of the transfer of the texture to the conduit. An exemplary polymeric film is polycarbonate. Other polymers, blends of polymers, and copolymers listed above can also be used to manufacture the template. Metals such as aluminum foil, copper foil and the like can be used to manufacture the template.

As noted above, the template may also be in the form of a tube that can be filled with a fluid. It is desirable for the tube to be capable of being wrapped around the conduit and being removed from it after effecting the transfer of the pattern to the conduit. In one embodiment, the tube can be inflated using a fluid such as, for example, air, water, volatile organic solvents, oils, and the like, or a combination comprising at least one of the foregoing fluids. Fluids that can be easily heated are desirable. Heated fluids can facilitate the heating of the template, which in turn can raise the temperature of the surface of the conduit above the softening point. The pressure and the temperature of the fluids can be controlled to vary the depth of the pattern in the surface of the conduit.

The conduit with the texture disposed thereon can be used in a wide variety of applications. The conduit is generally used in applications where it is used under water. The texture can also be disposed on conduits used in water filtration used in fresh and saline water treatment facilities. For example, it can be used on the inner and outer surfaces of pipes and hoses used to transfer water or other fluids, filters, nozzles, valves, heaters, granular particles, and the like.

The texture can also be disposed on surfaces that contact the mucous membranes of living beings. For example, it can be used on all surfaces that are contacted by the human mouth especially those surfaces that contact the mouths of toddlers. Examples of surfaces that are contacted by the mouths of toddlers are frames and supporting rods of high chair trays, pacifiers, diaper changing pads, crib frames and rails, reusable and disposable water bottles, cups and mugs, coffee thermos, toys, blocks, coins, and the like.

The texture can also be disposed on the surfaces of marine vessels and other devices that contact water. For example, it can be used on intake and outlet pipes for industrial and power plants, drilling rigs for underwater surfaces, conduits used in fish tanks and aquariums, bilge tanks, water treatment plants and pumping station surfaces—any surface inside such as in a water treatment plant and pumping station where organism growth and colonization is an issue. The pattern can be disposed on the surfaces of bags used to grow algae, for example, it can be used on the surface of a bag used to grow any microorganism but prevent attachment of the microorganism onto the surface of bag (medical or marine—e.g., blood bags where it is desirable to deter organism attachment to bag). Alternatively, by varying the surface texture or the size of the texture dimensions, it can be used on the surface of a bag used to grow any microorganism and encourage attachment of the microorganism to surface of the bag (e.g., a stem cell culture where it is desirable to encourage growth and attachment to surface).

The texture can also be used on the surfaces of body parts that are used in surgeries such as, for example, in a colostomy, and the like. The texture may also be used on the inner and outer surfaces of periodontal dressings; intravenous catheters and ports; foley catheters; surfaces in contact with tissues such as, for example, plates; adhesive tapes, patches, bandages, and the like; electronic leads; dental implants; orthodontia devices; iols (intraocular lenses); hydrogel films for tissue enhancement, skin grafting, isolation of bacteria or other microorganisms from tissues; heart-lung machine surfaces to reduce infection, clotting/thrombosis, enhance flow; tissue constructs for organ/tissue genesis; dialysis machine components, tubing and control panels; cochlear/otolaryngology implants and electronic devices; pace maker leads and body; fibrillator leads and body; heart valve flow surfaces and fixation surfaces; spinal implants; cranial/facial implants; biomedical instruments such as, for example, heart valves; scalpels; tongs; forceps; saws; reamers; grippers; spreaders; pliers; hammers; drills; laryngoscopes; bronchoscopes; oesophagoscopes; stethoscopes, mirrors, oral/ear speculum, xray plates/frames, xray device surfaces, magnetic resonance imaging (MRI) surfaces, echo cardiogram surfaces, cat-scan surfaces, scales, clipboards, and the like.

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method comprising:
    transporting a conduit and a template through a guide tube, the template being disposed on an outer surface of the conduit between the conduit and the guide tube;
    centering the conduit in the guide tube via a centering device;
    guiding the conduit into the guide tube via a conical guide that communicates with the guide tube; and
    transferring a texture from the template to the conduit as the conduit and the template are transported through the guide tube, wherein the template is in the form of a single film that is wrapped around the entire circumference of the conduit, and wherein the conduit is a catheter.

2. The method of claim 1, further comprising pressurizing the template, conduit, or the guide tube.

3. The method of claim 2, wherein the pressurizing the conduit or the template is accomplished by increasing fluid pressure within the conduit or within the template.

4. The method of claim 1, further comprising unwrapping the template after the transferring of the texture is completed.

5. The method of claim 1, further comprising curing the texture on the conduit.

6. The method of claim 5, wherein the curing is accomplished by heat and/or by radiation.

7. The method of claim 1, wherein the texture comprises a plurality of patterns.

* * * * *